US006615829B2

(12) United States Patent
Horn et al.

(10) Patent No.: US 6,615,829 B2
(45) Date of Patent: Sep. 9, 2003

(54) FEEDING APPARATUS FOR BREATHING MASKS THAT ALLOWS FOOD AND DRINK INTAKE WHEN THE MASK IS IN USE

(75) Inventors: Michael Horn, Berlin (DE); Klaus Schmidtke, Berlin (DE)

(73) Assignee: Auergeselischaft GmbH, Berlin (DE)

( * ) Notice: Subject to any disclaimer, the term of this patent is extended or adjusted under 35 U.S.C. 154(b) by 0 days.

(21) Appl. No.: 09/801,108

(22) Filed: Mar. 5, 2001

(65) Prior Publication Data

US 2002/0026142 A1 Feb. 28, 2002

(30) Foreign Application Priority Data

Mar. 8, 2000 (DE) .................................... 200 04 836 U

(51) Int. Cl.[7] ............................................. A61M 15/00

(52) U.S. Cl. .................. 128/202.15; 222/528; 222/490; 285/226; 141/338; 220/202; 137/223; 137/232; 128/206.21; 128/206.22; 128/201.26; 128/201.78; 128/205.24; 128/203.23; 251/149.6

(58) Field of Search ........................ 128/202.15, 206.22, 128/206.21, 201.28, 201.26, 201.27, 205.24, 203.23; 604/910, 99.04; 222/528, 490; 285/226; 141/338; 220/202; 137/223, 232; 251/149.6

(56) References Cited

U.S. PATENT DOCUMENTS

| | | | | |
|---|---|---|---|---|
| 4,537,189 A | * | 8/1985 | Vicenzi | 128/202.13 |
| 5,894,872 A | * | 4/1999 | Gale | 141/368 |
| 2003/0057237 A1 | * | 3/2003 | Stull et al. | 222/490 |

* cited by examiner

*Primary Examiner*—Glenn K. Dawson
*Assistant Examiner*—Mark Rademacher
(74) *Attorney, Agent, or Firm*—Welsh & Katz, Ltd.

(57) ABSTRACT

A feeding valve having a hose coupling in the form of an expansion bellows which unfolds automatically into the wearer's field of vision when the sealing cap of the feeding valve is opened, thereby enables a wearer to easily insert the straw of a food or beverage bottle even when wearing protective gloves.

1 Claim, 1 Drawing Sheet

FEEDING APPARATUS FOR BREATHING MASKS THAT ALLOWS FOOD AND DRINK INTAKE WHEN THE MASK IS IN USE

FIELD OF THE INVENTION

This invention relates to a feeding apparatus for breathing masks that allows food and drink intake when the mask is in use, does not reduce the wearer's field of vision, requires little space, and is protected from dirt and contamination.

BACKGROUND OF THE INVENTION

The state of the art includes solutions in which feeding valves are equipped with a drinking hose, and wherein said drinking hose can be moved into the mask wearer's field of vision (see, for example, U.S. Pat. No. 3,645,261). The disadvantages of such a solution are that there is a risk of dirtying and contamination if the feeding apparatus is opened and a risk of damaging the hose in use.

Another solution to reduce susceptibility to contamination would be the use of a sealed mask bag that houses the drinking hose. Such a solution, however, makes it less user-friendly as it is difficult to take the hose out of the bag when wearing protective gloves.

Breathing masks are used in practice that feature a feeding valve for food intake without a hose being connected to the mask. Such solutions have been described in DE 37 08 077 A1, DE-OS 23 21 607, and DE-OS 23 21 344. But these solutions require the wearer of the mask to insert the drinking hose that comes with the food bottle into the feeding valve without being able to see it, and so accidental contact with the breathing mask and the risk of dirtying and contamination cannot be ruled out.

SUMMARY OF THE INVENTION

It is a feature of this invention to provide a feeding apparatus for breathing masks that is not equipped with a drinking hose, does not reduce the wearer's field of vision, is protected from dirt and contamination and allows for contamination-free insertion of a drinking hose, if required.

The object of this invention was to provide a low cost and safe solution for a feeding apparatus of a breathing mask.

This problem of the invention was solved in that a hose coupling 3 in the form of an expansion bellows unfolds automatically into the wearer's field of vision when sealing cap 1 of the feeding valve 2 is opened, which enables a wearer to easily insert the straw of a food or beverage bottle even when wearing protective gloves.

Placing the feeding apparatus of the invention behind the sealing cap of the feeding valve and compressing the hose coupling like a bellows provides excellent protection from dirt and contamination, prevents the apparatus from reducing the mask wearer's field of vision and makes it fit into a very small installation space when closed.

Figure 1:
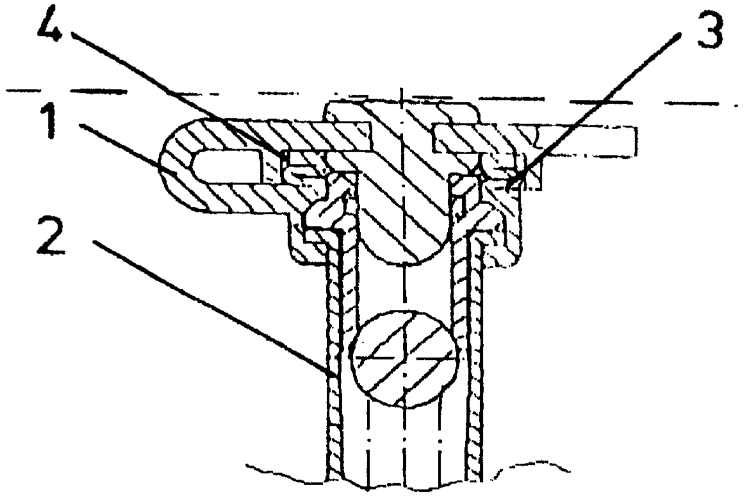
Figure 2:
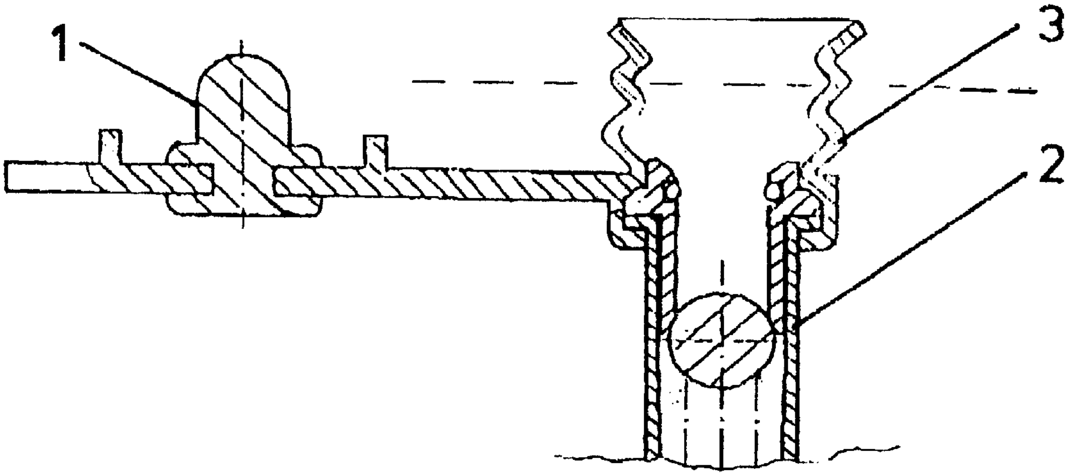

The invention shall be explained in greater detail based on an embodiment that is shown in FIGS. 1 and 2 below.

DESCRIPTION OF THE DRAWING FIGURES

FIG. 1 shows the feeding apparatus according to the invention when the feeding valve 2 is closed. The expansion bellows of the hose coupling 3 is compressed into a chamber 4 of said feeding valve 2. The feeding valve 2 is sealed gas-tight by the sealing cap 1.

FIG. 2 shows the feeding apparatus according to the invention when the feeding valve 2 is open. The expansion bellows 3 has been released and is now ready for easy insertion of the straw of a food or beverage bottle into a feeding valve 2 through hose coupling 3.

A suitable material for the hose coupling 3 is butyl rubber, and the chamber 4 can be made either from butyl rubber or a glass fiber reinforced polyamide.

In another embodiment, the feeding apparatus with the self-releasing hose coupling 3 can also be combined with a pivotable feeding valve inside the chamber 4. This solution overcomes the disadvantages of the state of the art.

The solution accordingly to the invention requires only little space when closed, and the hose coupling 3 is well visible to the mask wearer when the apparatus is open. This applies to any shapes of faces, eye positioning, and mask size.

We claim:

1. A feeding apparatus for a breathing mask that permits food and drink intake during use, having an elastic extendible and compressible expansion bellows in the form of a hose coupling, said bellows having a free unattached end extending from the opening of a feeding valve in an opened position; and a sealing cap forming a cavity to receive the free unattached end compressed bellows in a closed position, said cavity releasing said compressed expansion bellows from said closed position after removal of said sealing cap, to said open position thereby exposing said bellows for use in insertion of a food and drink tube.

* * * * *